US010828105B2

(12) United States Patent
Sahay et al.

(10) Patent No.: US 10,828,105 B2
(45) Date of Patent: Nov. 10, 2020

(54) SYSTEM AND METHODS FOR ABLATION TREATMENT PLANNING AND INTRAOPERATIVE POSITION UPDATES OF ABLATION DEVICES

(71) Applicant: ENDOCARE, INC., Austin, TX (US)

(72) Inventors: Alind Sahay, West Chester, PA (US); Robert J. Riker, Sewickley, PA (US); Cristian Atria, Salt Lake City, UT (US)

(73) Assignee: Endocare, Inc., Austin, TX (US)

( * ) Notice: Subject to any disclaimer, the term of this patent is extended or adjusted under 35 U.S.C. 154(b) by 204 days.

(21) Appl. No.: 15/128,372

(22) PCT Filed: Mar. 23, 2015

(86) PCT No.: PCT/US2015/022010
§ 371 (c)(1),
(2) Date: Sep. 22, 2016

(87) PCT Pub. No.: WO2015/148378
PCT Pub. Date: Oct. 1, 2015

(65) Prior Publication Data
US 2017/0209218 A1    Jul. 27, 2017

Related U.S. Application Data

(60) Provisional application No. 61/969,132, filed on Mar. 22, 2014.

(51) Int. Cl.
*A61B 18/12*    (2006.01)
*A61B 34/10*    (2016.01)
(Continued)

(52) U.S. Cl.
CPC .............. *A61B 34/10* (2016.02); *A61B 6/032* (2013.01); *A61B 6/487* (2013.01); *A61B 6/5235* (2013.01);
(Continued)

(58) Field of Classification Search
CPC .......... A61B 18/02; A61B 2018/00511; A61B 2018/00541; A61B 2018/00577;
(Continued)

(56) References Cited

U.S. PATENT DOCUMENTS 5,694,170 A    12/1997    Tiwari et al.
6,445,957 B1 *  9/2002    Bolmsjo ................ A61B 18/00
                                                                  606/29

(Continued)

FOREIGN PATENT DOCUMENTS

WO    WO 2010/075305    7/2010

OTHER PUBLICATIONS

European Supplementary Search Report, dated Oct. 11, 2017, in EP Patent Application No. 15769484.5.
(Continued)

*Primary Examiner* — Daniel W Fowler
(74) *Attorney, Agent, or Firm* — Duane Morris LLP; Manita Rawat

(57) ABSTRACT

A system for assisting a surgeon in placing at least one ablation device into a treatment region of a patient, where the system includes at least one computer system having a display, a user interface and software, is described. The system uses patient image data of the treatment region to generate an image of the treatment region on the display and identifies the treatment region to ablate with a target. Tissue properties of the treatment region are identified and used to perform thermal modeling. Treatment parameters are generated and an ablation zone is calculated. A computer system
(Continued)

display is generated showing (a) the number of ablation devices required to ablate the treatment region and the location and orientation of each ablation device in the treatment region and (b) the ablation zone.

20 Claims, 13 Drawing Sheets

(51) Int. Cl.
*A61B 6/00* (2006.01)
*A61B 34/00* (2016.01)
*A61B 6/03* (2006.01)
*A61B 18/02* (2006.01)
*A61B 18/00* (2006.01)
*A61B 90/00* (2016.01)

(52) U.S. Cl.
CPC .............. *A61B 18/02* (2013.01); *A61B 34/25* (2016.02); *A61B 2018/00511* (2013.01); *A61B 2018/00541* (2013.01); *A61B 2018/00577* (2013.01); *A61B 2018/00642* (2013.01); *A61B 2018/00982* (2013.01); *A61B 2018/0293* (2013.01); *A61B 2034/104* (2016.02); *A61B 2034/105* (2016.02); *A61B 2034/107* (2016.02); *A61B 2090/3764* (2016.02)

(58) Field of Classification Search
CPC ........... A61B 2018/00642; A61B 2018/00982; A61B 2018/0293; A61B 2034/105; A61B 2034/107; A61B 2090/3764; A61B 34/10; A61B 34/25; A61B 6/032; A61B 6/487; A61B 6/5235
See application file for complete search history.

(56) References Cited

U.S. PATENT DOCUMENTS

| | | | |
|---|---|---|---|
| 6,575,969 B1* | 6/2003 | Rittman, III | A61B 18/1482 128/898 |
| 8,187,260 B1 | 5/2012 | Bao | |
| 8,187,269 B2 | 5/2012 | Shadduck et al. | |
| 8,591,503 B2 | 11/2013 | Littrup et al. | |
| 2003/0078490 A1* | 4/2003 | Damasco | A61B 18/02 600/407 |
| 2006/0155267 A1* | 7/2006 | Berzak | A61B 18/02 606/20 |
| 2007/0219448 A1* | 9/2007 | Seip | A61B 8/06 600/454 |
| 2008/0033417 A1* | 2/2008 | Nields | A61B 18/18 606/27 |
| 2008/0154253 A1 | 6/2008 | Damasco et al. | |
| 2009/0048515 A1* | 2/2009 | Suri | A61B 8/12 600/443 |
| 2009/0221999 A1* | 9/2009 | Shahidi | A61B 18/18 606/33 |
| 2010/0168725 A1* | 7/2010 | Babkin | A61B 18/02 606/21 |
| 2011/0251607 A1* | 10/2011 | Kruecker | A61B 18/1206 606/34 |
| 2012/0237105 A1* | 9/2012 | Mielekamp | G06T 19/00 382/132 |
| 2012/0271376 A1 | 10/2012 | Kokones et al. | |
| 2013/0184696 A1* | 7/2013 | Fourkas | A61B 18/02 606/24 |
| 2013/0317363 A1 | 11/2013 | Case et al. | |

OTHER PUBLICATIONS

Chinese Office Action, dated Jan. 15, 2020, in CN Patent Application No. 201580014675.4.

* cited by examiner

FIG. 12

SYSTEM AND METHODS FOR ABLATION TREATMENT PLANNING AND INTRAOPERATIVE POSITION UPDATES OF ABLATION DEVICES

CROSS-REFERENCE TO RELATED APPLICATIONS

This application claims the benefit of U.S. Provisional Application No. 61/969,132, filed Mar. 22, 2014, the contents of which are incorporated herein by reference in their entirety for all purposes.

TECHNICAL FIELD

Embodiments of the present invention relate generally to tissue ablation and, in particular, tissue ablation planning, guidance and treatment systems for performing computer guided ablative surgery.

BACKGROUND

In current computer guided ablation treatment planning and guidance systems, an initial treatment plan is prepared that defines the area in the human body to be treated (cancerous tissue, abnormal cells, lesions, and organs, such as, for example, the prostate, breast, liver, lung, kidney, bone, etc.) (the "treatment region"). These treatment planning and guidance systems then allow the physician/clinician to manually identify the positioning and locations of ablation devices, such as, for example, cryoprobes, cryoneedles, optical fibers, radio frequency (RF) needles/electrodes, electrodes, microwave antennas, etc., with respect to the treatment region. With these systems, the clinician must estimate lethal ablation zones as well as the safety margins surrounding the lethal ablation zones and treatment margins surrounding the treatment region. In addition, when ablation devices, such as cryoprobes, are inserted through the skin and into the treatment region, the cryoprobes and any positioning devices that are used may flex and the organ or other body tissue may also shift or move in response to the ablation device insertion. Therefore, the final position of the ablation device in the treatment region may be different from the planned position that was included in the treatment plan, resulting in different lethal ablation zones as well as different ablation margins than originally planned.

Additionally, the initial treatment plan may be prepared in the clinician's office with an initial image data-set provided by the patient, which may be different from the image data-set that is used by the clinician during the time of the ablation procedure. Therefore, it is advantageous for the ablation system to provide for a way to register the location of the treatment region between two or more different data sets. Furthermore, during the procedure, the clinician may be working between two or more different locations, for example, the interventional radiology (IR) suite and the control room. Accordingly, the system needs to provide for concurrent updates of the treatment plans and the guided ablation device positions in multiple different locations.

Moreover, although the clinician has prepared an initial treatment plan that outlines where the ablation devices should be positioned in the human body, e.g., the treatment region, it is difficult for the clinician to insert the ablation devices in the exact location and at the exact orientation as planned. Factors that affect an ablation device's final position in the human body include, but are not limited to, insertion point through the skin and angle of insertion. Because of these variables, it is challenging for a clinician to precisely position the ablation devices as planned. As will be readily understood by those skilled in the art, proper positioning of the ablation devices leads to better and more predictable procedure outcomes.

Current computer guided cryosurgery systems include those described in commonly-assigned U.S. Pat. Nos. 5,531,742; 5,647,868; 6,139,544; 6,485,422; 6,544,176; 6,643,535; 7,363,071; 8,187,260; and 2008/0154253, the entire contents of each of the aforementioned U.S. Patents and Publications are incorporated herein by reference in their entirety for all purposes.

In order to address the above-discussed potential problems and issues with current computer guided ablation planning, guidance and treatment systems, disclosed and described herein are systems and methods that, inter alia, allow a clinician/physician to more accurately prepare an ablation treatment plan and provide better treatment guidance during the ablation procedure.

SUMMARY

Embodiments of the present invention are directed to a system for assisting a surgeon in placing at least one ablation device into a treatment region of a patient, where the system includes at least one computer system comprising a display, a user interface and software. The software is configured to receive patient image data of the treatment region, generate an image of the treatment region on the display, identify the treatment region to ablate with a target, identify tissue properties of the treatment region, perform thermal modeling of the treatment region based on the tissue properties of the treatment region, generate treatment parameters for the at least one ablation device, calculate a number of ablation devices required to ablate the treatment region and a location and orientation of each ablation device in the treatment region based on a size of the target and the thermal modeling of the treatment region performed based on the tissue properties of the treatment region, calculate an ablation zone based on the number of ablation devices required to ablate the treatment region and the location and orientation of each ablation device in the treatment region, and display on the computer system display (a) the number of ablation devices required to ablate the treatment region and the location and orientation of each ablation device in the treatment region and (b) the ablation zone.

Embodiments of the present invention are also directed to a method of developing an ablation treatment plan where the method includes the steps of receiving patient image data of a treatment region, generating an image of the treatment region on a display, identifying the treatment region to ablate with a target, identifying tissue properties of the treatment region, performing thermal modeling of the treatment region based at least in part on the thermal properties of the tissue in the treatment region, determining treatment parameters for at least one ablation device, calculating a number of ablation devices required to ablate the treatment region and a location and orientation of each ablation device in the treatment region based on a size of the target and the thermal modeling of the treatment region performed based on the tissue properties of the treatment region, calculating an ablation zone based on the number of ablation devices required to ablate the treatment region and the location and orientation of each ablation device in the treatment region, and displaying on the display (a) the number of ablation devices required to ablate the treatment region and the location and orientation of each ablation device in the treatment region and (b) the ablation zone.

In another embodiment of the present invention, a system for guiding and performing an ablation procedure on a treatment region of a patient is provided. The system includes at least one computer system having a display, a user interface and software, where the computer system configured to receive an ablation treatment plan comprising (a) a treatment plan set of patient image data, (b) a number of ablation devices required to ablate the treatment region and the location and orientation of each ablation device in the treatment region and (c) boundaries of an ablation zone. The computer system is also configured to (a) receive at least one set of patient image data of the treatment region taken on a day of the ablation procedure, (b) register the at least one set of patient image data of the treatment region taken on the day of the ablation procedure to the treatment plan set of patient image data, (c) allow adjustment of a size and/or shape and/or location of the treatment region based on the registered at least one set of patient image data of the treatment region taken on the day of the ablation procedure to the treatment plan set of patient image data, (d) recalculate the number of ablation devices required to ablate the treatment region and the location and the orientation of each ablation device in the treatment region based on any adjustments to the size and/or shape and/or location of the target based on the registered first set of patient image data and the second set of patient image data, (e) update the ablation zone based on the recalculated number of ablation devices required to ablate the treatment region and/or the recalculated location and/or the recalculated orientation of each ablation device in the treatment region, and (f) update the display on the computer system to display (i) the recalculated number of ablation devices required to ablate the treatment region and/or the recalculated location and/or the recalculated orientation of each ablation device in the treatment region and (ii) the remodeled ablation zone. The system also includes an ablation energy generator and at least one ablation device.

For a better understanding of the embodiments of the present invention, its operating advantages and specific objects attained by its uses, reference is made to the accompanying descriptive matter in which preferred embodiments of the invention are illustrated in the accompanying drawings.

BRIEF DESCRIPTION OF THE FIGURES

FIG. 12 depicts a three-view image on a computer device display of a treatment planning and guidance system showing insertion of two cryoprobes and the resulting combined/composite cryoprobe isotherms, according to an embodiment of the present invention.

DETAILED DESCRIPTION

Figure 1:
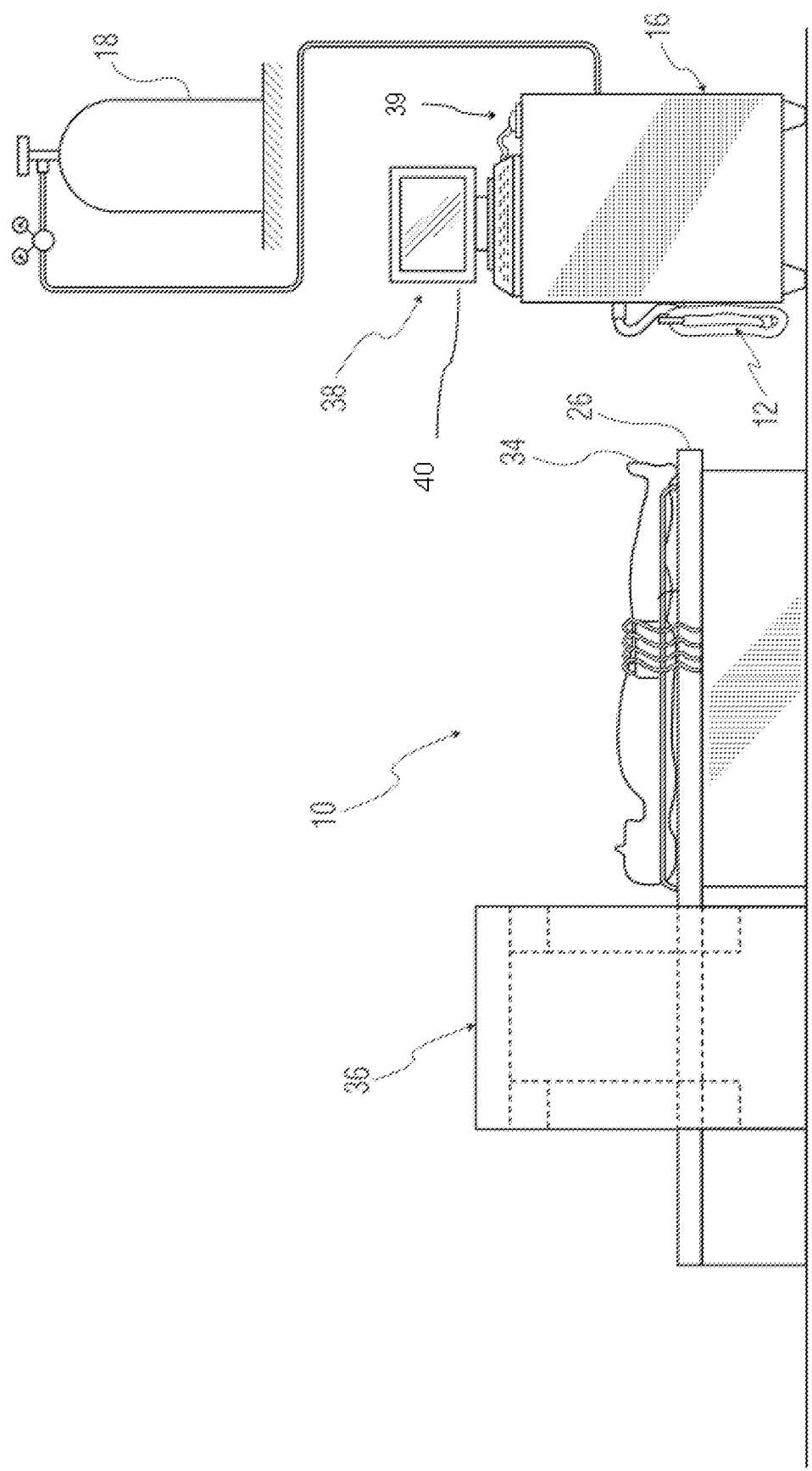
FIG. 1 is a system schematic of an ablation system, according to an embodiment of the present invention.

Embodiments of the present invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements. Features disclosed as belonging to certain embodiments can be used with other embodiments of the invention disclosed herein.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the disclosed invention. For example, as used in the specification including the appended numbered paragraphs, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein. And any dimensions shown in the attached drawings are representative and not limiting of the invention, as larger or smaller dimensions can be used as desired.

It will also be understood that, although the terms first, second, etc. may be used herein to describe various elements, these elements should not be limited by these terms. These terms are only used to distinguish one element from another. Thus, a first element could be termed a second element without departing from the teachings of the embodiments of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In embodiments of the present invention disclosed and described herein, the ablative devices are cryosurgical probes and the ablation procedures are cryoablation surgery. However, it is understood that various other types of ablative devices may be used in accordance with the principles of the embodiments of the present invention to provide the necessary ablation procedure. The ablative devices may comprise, for example, RF needles/electrodes, laser fibers, optical fibers, microwave catheters and antennas, electrodes, high-intensity focused ultrasound devices, and other suitable ablative devices. In addition, although the ablation procedure discussed and depicted herein is for a kidney ablation, the systems disclosed and described herein, can be used to perform ablation procedures on other body tissue and organs, such as, for example, the prostate, liver, lung, breast, skin, bone, cervix, endometrium, the cardiovascular system including the heart, the nervous system, cancerous tissue, abnormal cells, etc. Moreover, clinician, physician and surgeon are used interchangeably. Those of skill in the art readily understand that embodiments of the present invention can be used by any health care professional that can perform any of the ablation procedures disclosed herein Referring now to the drawings and the characters of reference marked thereon, FIG. 1 illustrates a cryosurgical system according to an embodiment of the present invention, designated generally as 10. The cryosurgical system 10 includes a fluid supply line 12 that is connected to a cryoengine 16 that supplies cryogenic fluid for the procedure. In some embodiments, the cryogenic fluid is provided by a fluid source 18. In some embodiments, the cryogenic fluid may be nitrogen, argon or any other fluid capable of providing a cryogenic effect in body tissue. FIG. 1 illustrates a patient 34 positioned on a table 26 adjacent to an imaging device 36. In addition, the cryosurgical system 10 includes a computer device 38 that is programmed with software configured to run an ablation planning, guidance and treatment system, e.g., the computer device 38 can run or access and update/revise an ablation treatment plan and can also provide treatment guidance as well as run the ablation devices during the ablation procedure. In addition to being programmed with software configured to run an ablation planning, guidance and treatment system, the computer device 38 also includes at least one user interface 39, a display 40 and a processor. It should be noted that prior to this point in the procedure, the clinician/physician has already prepared an initial ablation treatment plan, which will be discussed in more detail below.

Figure 2:
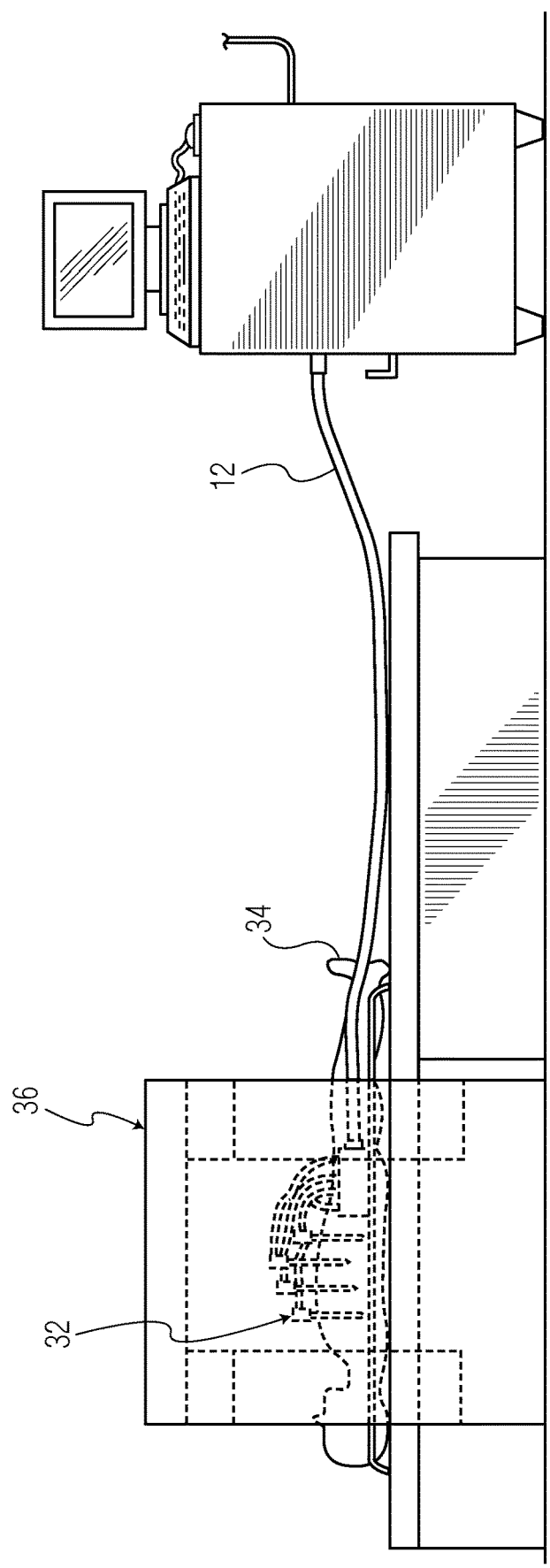
FIG. 2 depicts a patient inserted into an imaging device during ablation device placement, according to an embodiment of the present invention.

As will also be discussed in more detail below, in some embodiments of the present invention, during the ablation procedure, as depicted in FIG. 2, the patient 34 is introduced into the imaging section of the imaging device 36 multiple times during insertion of the cryoprobes 32 as part of the treatment guidance process to insure that the cryoprobes 32 are being placed in accordance with the ablation treatment plan that was previously prepared. As also discussed below, if the clinician determines that, as a result of the additional image data sets that are obtained during the ablation procedure, the cryoprobes are not being placed according to the treatment plan, the clinician can update and revise the treatment plan to compensate for these deviations.

In some embodiments, the imaging device 36 can be, for example, CT, MRI, PET, SPECT, X-ray (including fluoroscope), ultrasound or other suitable imaging devices. The imaging device 36 receives imaging data from the treatment region of the patient 34 during the ablation procedure. The treatment region may be, for example, any region in the human body including, the prostate region, breast region, liver region, lung region, kidney region, heart region, bone, cancerous tissue or lesions, other organs, nerves, etc. The imaging device can be, for example, a non-integrated device with the capability of taking 3D fluoro shots of the treatment region or it can be an integrated system where the clinician or user can identify the position of the cryoprobes relative to an organ, boney structure or other identified fiducial data in an image set in real-time, such as, for example, an ultrasound probe.

Turning now to the ablation planning, guidance and treatment system, in some embodiments of the present invention, the system comprises one or more computer devices that may be networked together and programmed with software configured to display 2D and 3D image data. The software may also be configured to display models of the cryoprobes/ablation devices and isotherm/ablation zone information. At least one of the computer devices, which may be the primary ablation computer 38, is capable of operating an ablation energy device, such as, for example, a cryoengine 16, in order to deliver energy/cryogen to the treatment region. Additional ablation energy devices include, and are not limited to, radio frequency generators, laser energy generators, microwave generators and high-intensity focused ultrasound generators.

The system also includes software configured to perform the ablation planning, guidance and treatment functions disclosed and described herein. Prior to the ablation procedure, a clinician utilizes the system's treatment planning capabilities to prepare an ablation treatment plan. To prepare this plan, the clinician begins by uploading patient image data of the treatment region provided by one of the above-discussed imaging devices into the planning system. The patient image data may be provided in electronic form by the patient or may be uploaded from a picture archiving and communication system ("PACS"). In one embodiment, the patient image data is in the form of a CT scan.

Figure 3:
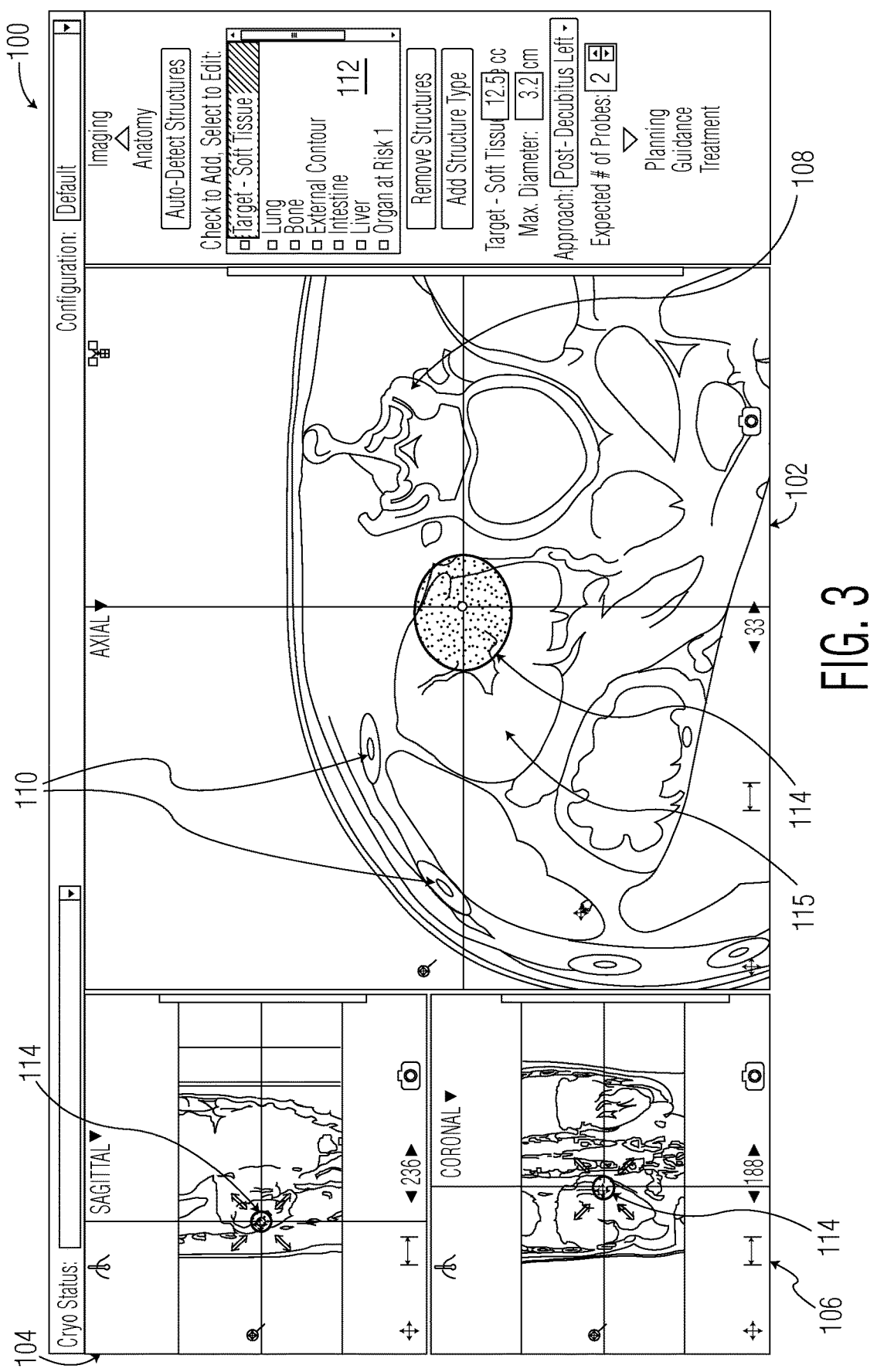
FIG. 3 depicts a three-view image on a computer device display of a treatment planning and guidance system, according to an embodiment of the present invention.

After the patient image data is uploaded to the planning system, the system is configured to produce a three-view image 100 on the computer device display as depicted in FIG. 3. The three-view image 100 includes an axial view 102, a sagittal view 104 and a coronal view 106. The position of each view on the screen can be changed by the clinician. For example, if the clinician prefers to have the sagittal view as the main view, the planning system allows the clinician to rearrange the location of the views on the display. As can be seen in FIG. 3, certain patient anatomy such as spine vertebrae 108 and ribs 110 can be identified in the three-view image 102. These are structures/anatomy that the clinician may need to avoid during the ablation procedure both during placement of the ablation devices or cryoprobes as well as to ensure that the ablation zone does not extend to these structures/anatomy. In addition, the clinician can specifically mark certain anatomy on the CT scan to avoid during the procedure. For example, the planning system allows the clinician to identify a patient's lungs by choosing the lung feature in the selection box 112 on the right side of the screen, which includes a drop down box to allow a clinician to select various anatomy from an anatomy library included with the system. Once chosen, the clinician can outline the lungs on the axial view 102 using any user interface device known to those of skill in the art including, but not limited to, an electronic pen, a mouse, etc., allowing the lungs to be clearly identified during the ablation procedure. Once outlined in the axial view 102, the system automatically marks and identifies the corresponding anatomy on the sagittal view 104 and coronal view 106. The clinician can also specifically identify any other anatomy included in the anatomy library such as, for example, bone, the liver, the intestines, etc.

With the CT scan or image data set uploaded to the planning system and displayed in the three-view format 100, the clinician can now identify the treatment region with a target 114. The target 114 is identified and delineated by the clinician using any of a number of fast/intuitive methods, one of which is to use predefined target shapes and locate the target shape centrally in the target region and then adjust using "intuitive handles." The target 114 can be any size or geometric shape so that it completely covers/identifies the treatment region. Other embodiments of fast/intuitive methods for target definition include atlas shapes from a library of shapes that are automatically morphed using image density information to the shape of the lesion/target region. These morphing methods could have various user interface methods/devices to allow the clinician to adjust the size, shape or location of the target 114 in 3D or in planes with shape updates based on 3D reconstruction algorithms. As can be seen in FIG. 3, the treatment region is a portion of the kidney 115 and the target 114 is in the form of an oval. Once the target 114 is positioned on the axial view 102, its corresponding location on the sagittal view 104 and coronal view 106 is generated automatically by the system. In some cases, the clinician may need a better view or a different view of the treatment region than what was initially presented on the screen by the system. In these cases, the clinician can rotate or change the orientation of the axial view 102, which will also cause the sagittal view 104 and coronal view 106 to rotate or reorient in a corresponding manner. As a result of the three views being presented simultaneously on the same screen, the clinician is able to obtain what is essentially a 3D view of the treatment region, which results in a better and more accurate visualization of the treatment region. Because the clinician can change the orientation/viewing angle of the three views and can also change the size, shape and location of the target 114 on each of the three views, the clinician can essentially 3D model the target 114 to ensure complete and accurate target destruction during the ablation procedure while avoiding damage to surrounding tissue/anatomy.

In addition to identifying anatomy that a clinician may want to avoid during an ablation procedure, the planning system allows the clinician to identify the specific anatomy and tissue type in the treatment region as well as anatomy and tissue type surrounding the treatment region all of which may affect cryoprobe isotherms and hence, lethal ice formation during a cryoablation procedure. Certain tissue types have specific thermal properties such as, for example, heat capacity, thermal conductivity, transfer rate, density, perfusion, metabolic heat generation, etc., which may affect the thermal properties of the tissue in the treatment region and the tissue surrounding treatment region. Because the tissue surrounding the treatment region can affect the thermal properties of the tissue within the treatment region, it is important to be able to identify this tissue as well. Therefore, the planning system includes a module 116 (depicted in FIG. 4) with a tissue property database/library of different tissue types and their associated tissue properties. This gives a clinician the ability to further model the treatment plan in more detail by identifying tissue types within the treatment region as well as the tissue types surrounding the treatment region and including them in the treatment plan.

Figure 4:
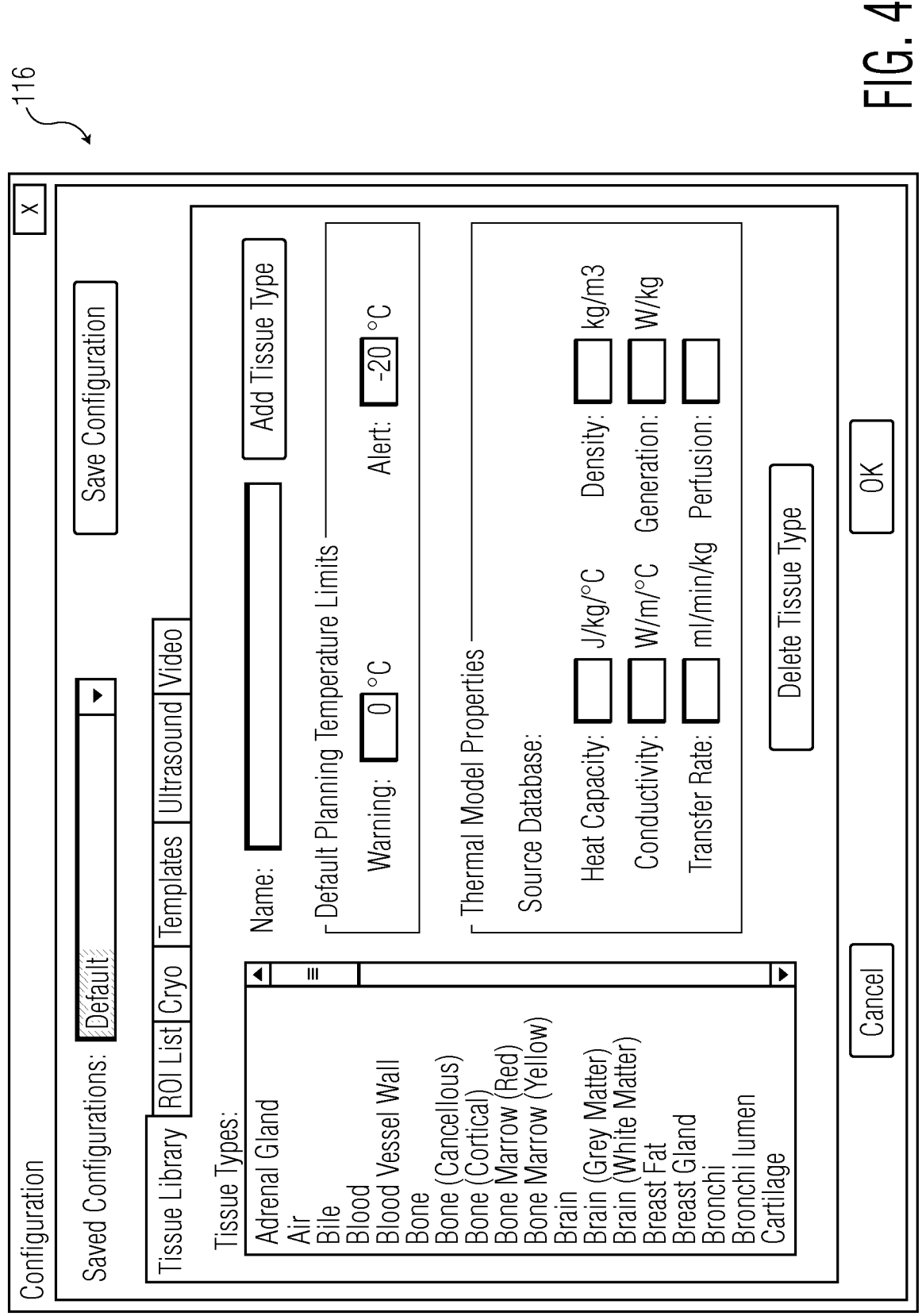
FIG. 4 depicts an image on a computer device display of a tissue characteristics library of a treatment planning and guidance system, according to an embodiment of the present invention.

Thus, for example, if the clinician is performing a cryoablation procedure on a tumor in a bronchi lumen, the bronchi lumen would be identified with the target 114 and the physician would highlight or select the target and would choose "Bronchi lumen" from the "Tissue Types" dropdown box depicted in FIG. 4 at which point, the system populates the associated tissue properties for bronchi lumen such as heat capacity, thermal conductivity, transfer rate, density, perfusion, and metabolic heat generation. Additionally, to get a more accurate thermal model of the treatment region, the clinician could identify additional tissue types in the vicinity of the bronchi lumen such as, for example, a breast gland. To do this, the clinician would identify the breast gland on the three-view image using a user interface such as any of those disclosed herein, and would then choose "Breast Gland" from the "Tissue Types" dropdown box depicted in FIG. 4. After the "Breast Gland" tissue type is selected, the system populates the associated tissue properties for a breast gland such as heat capacity, thermal conductivity, transfer rate, density, perfusion, and generation. As a result of the system's ability to identify tissue types within the treatment region and surrounding a treatment region, the system can take the thermal tissue properties of all of the identified tissue types into consideration when calculating and developing the treatment plan. For example, for treatment region tissue and/or surrounding tissue with a high heat capacity, the planning system may develop a treatment plan with more cryoprobes, different cryoprobe placement, higher energy power settings, longer freeze times, etc., in order to compensate for these tissue properties. This allows a clinician to prepare a more accurate treatment plan because more accurate thermal modeling of the treatment region can be achieved. The thermal properties of the treatment region tissue and tissue surrounding the treatment region continue to be taken into account by the system when the treatment plan is updated or revised by the clinician (discussed in detail below) or during treatment guidance during the ablation procedure if the original treatment plan changes during the ablation procedure (also discussed in detail below).

The tissue property database includes the thermal properties of body tissue measured at body temperature. Unfortunately, these tissue properties vary with temperature, particularly at phase transitions. To compensate for this, in one embodiment of the present invention, the system models each of tissue properties as two linear functions of temperature, one below 0° C. and one above 0° C. Although there is no detailed information on the temperature dependence of these tissue properties for tissue types, we do, however, know how a tissue's thermal properties vary based on the tissue's water content. Therefore, the system can adjust the thermal properties of modeled tissue as the modeled temperature changes by inferring a contribution from the tissue's water content. The water temperature-based adjustments can be automatically applied to the tissue's thermal properties (heat capacity and density) as measured at body temperature according to inferences about the tissue composition derived from the existing tissue property database. Therefore, as the treatment region tissue's thermal properties and the surrounding tissue's thermal properties change during a procedure, for example, as a result of a drop in temperature due to freezing in the treatment region, the system can determine the effect this change has on the modeled isotherms.

Figure 5:
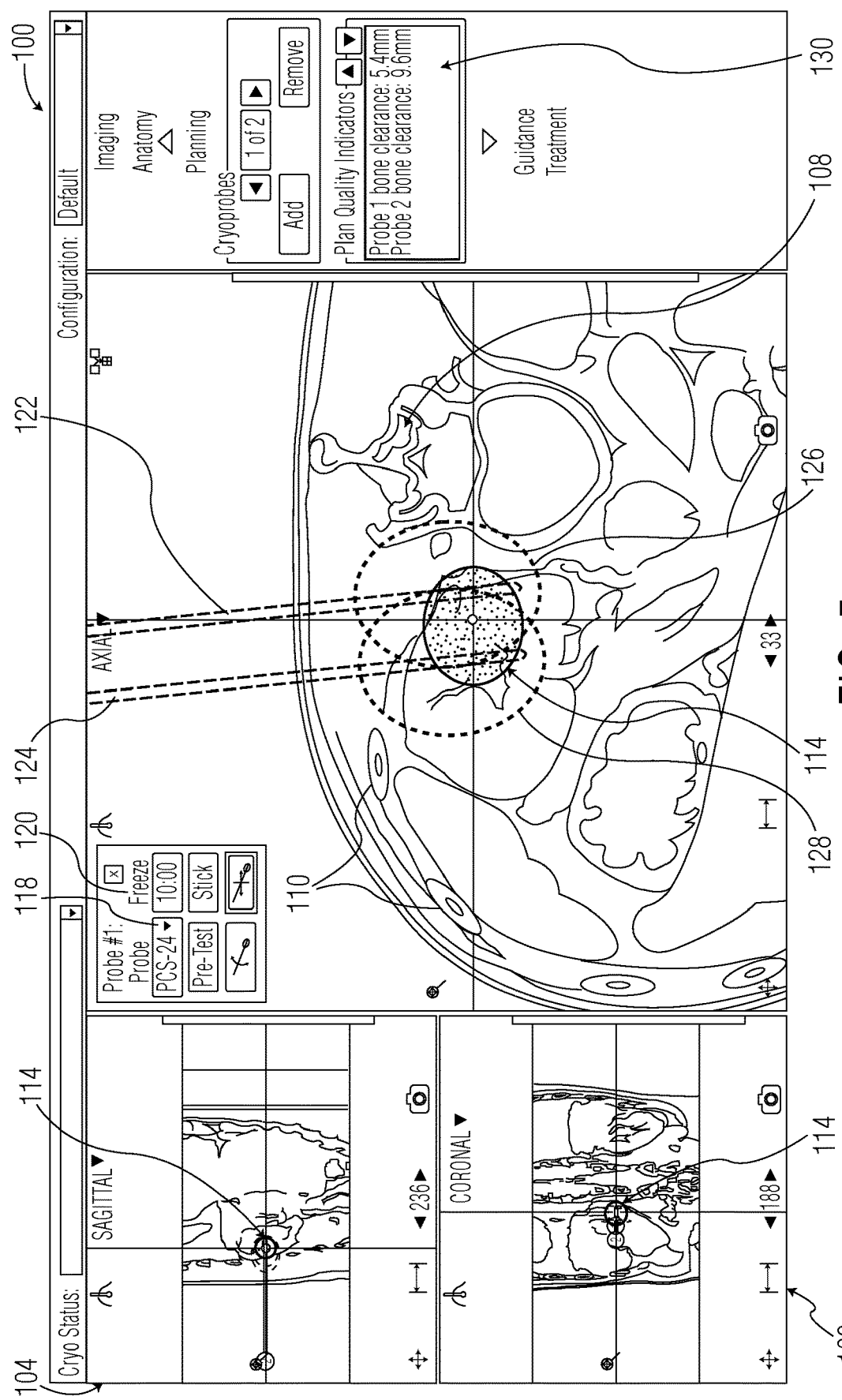
FIG. 5 depicts a three-view image on a computer device display of a treatment planning and guidance system showing individual isotherms for two separate cryoprobes, according to an embodiment of the present invention.

Turning now to FIG. 5, once the clinician has identified the treatment region and any additional surrounding anatomy of interest on the CT scan, the system determines recommended treatment parameters such as cryoprobe size 118 and freeze time 120, into the planning system. Other treatment parameters include, but are not limited to, freeze/thaw cycles and cycle times (e.g., ablation protocols such as 10 min. freeze, 8 min. thaw, and 10 min. freeze, etc.). At this point, the planning system is now ready to calculate/develop the treatment plan. As can be seen in FIG. 5, based on all of the anatomy identified on the CT scan, including the treatment region, all of the information entered into the system by the clinician including the identification of surrounding anatomy and tissue type, and any thermal modeling performed by the system based on the information in the tissue property database, the planning system has developed a treatment plan that includes two cryoprobes 122, 124 with the specific locations and orientations (insertion angles) in the treatment region identified in FIG. 5. The planning system has also calculated a power setting for each cryoprobe 122, 124 (not shown), which will be used by the treatment system during the ablation procedure. Based on the size of the target 114, the treatment parameters chosen by the clinician and the effect the surrounding anatomy and tissue type have on the treatment region, those of skill in the art readily understand that the number of ablation devices, (in this embodiment, cryoprobes), can change and is therefore, not limited to two as depicted in this embodiment of the present invention. The number of ablation devices (in this embodiment, cryoprobes), can range from as little as one to as many as eight.

As stated above, based on the clinician's identification of the treatment region with a target 114 and the clinician's identification of the target tissue and any surrounding anatomy of interest, the system calculates/generates a treatment plan (number of cryoprobes to use, location of cryoprobe insertion, and orientation of the cryoprobes) based on the treatment parameters recommended by the system. At this point, however, the clinician can change the treatment parameters such as cryoprobe size, freeze times, etc., based on the clinician's preference and/or experience. Any such changes to the treatment parameters results in the system recalculating a new treatment plan that may result in a change in the number of cryoprobes used, a change in the location of cryoprobe insertion, a change in cryoprobe orientation, a change in cryoprobe power settings, etc.

As can also be seen in FIG. 5, the planning system has identified an individual isotherm 126, 128 for each cryoprobe 122, 124, respectively, as well as calculated the distances of each cryoprobe 122, 124 from its closest boney structure (see the Plan Quality Indicators 130, which show that probe 1 (cryoprobe 122) is 5.4 mm from bone and probe 2 (cryoprobe 124) is 9.6 mm from bone). In some embodiments, in order to avoid damaging or encountering tissue and anatomy surrounding the treatment region, the planning system includes a database of Plan Quality Indicators of distances that the cryoprobes and isotherms must remain from certain anatomy. Safe distances may be identified by the Plan Quality Indicators being displayed in green, distances that may adversely affect surrounding anatomy may result in the Plan Quality Indicators being displayed in yellow, and distances most likely to cause damage to surrounding anatomy may result in the Plan Quality Indicators being displayed in red. Because of these Plan Quality Indicators, the treatment plan will, in most circumstances, incorporate cryoprobe placements that take into account the safe distances to surrounding tissue and anatomy thereby avoiding damage to the surrounding tissue and anatomy. In some embodiments, the Plan Quality Indicators may also reflect minimum or maximum temperatures in tissue or other anatomy (organs) at risk for damage. The Plan Quality Indicators can also be used to direct the clinician's attention to different image views on the display that may contain relevant information. That is, clicking or otherwise selecting a Plan Quality Indicator 130 that may be for example, yellow or red, can change the current view on the display to highlight the related relevant area in all of the image views, axial, sagittal and coronal, (e.g., point of closest approach, or min/max temperature) to show the clinician an area of concern that may not be viewable in the current view 102. These Plan Quality Indicators are also relevant during the treatment guidance phase when the clinician/physician may have to adjust cryoprobe placement to compensate for previously placed cryoprobes that may not have been inserted according to the treatment plan, as discussed below.

Figure 6:
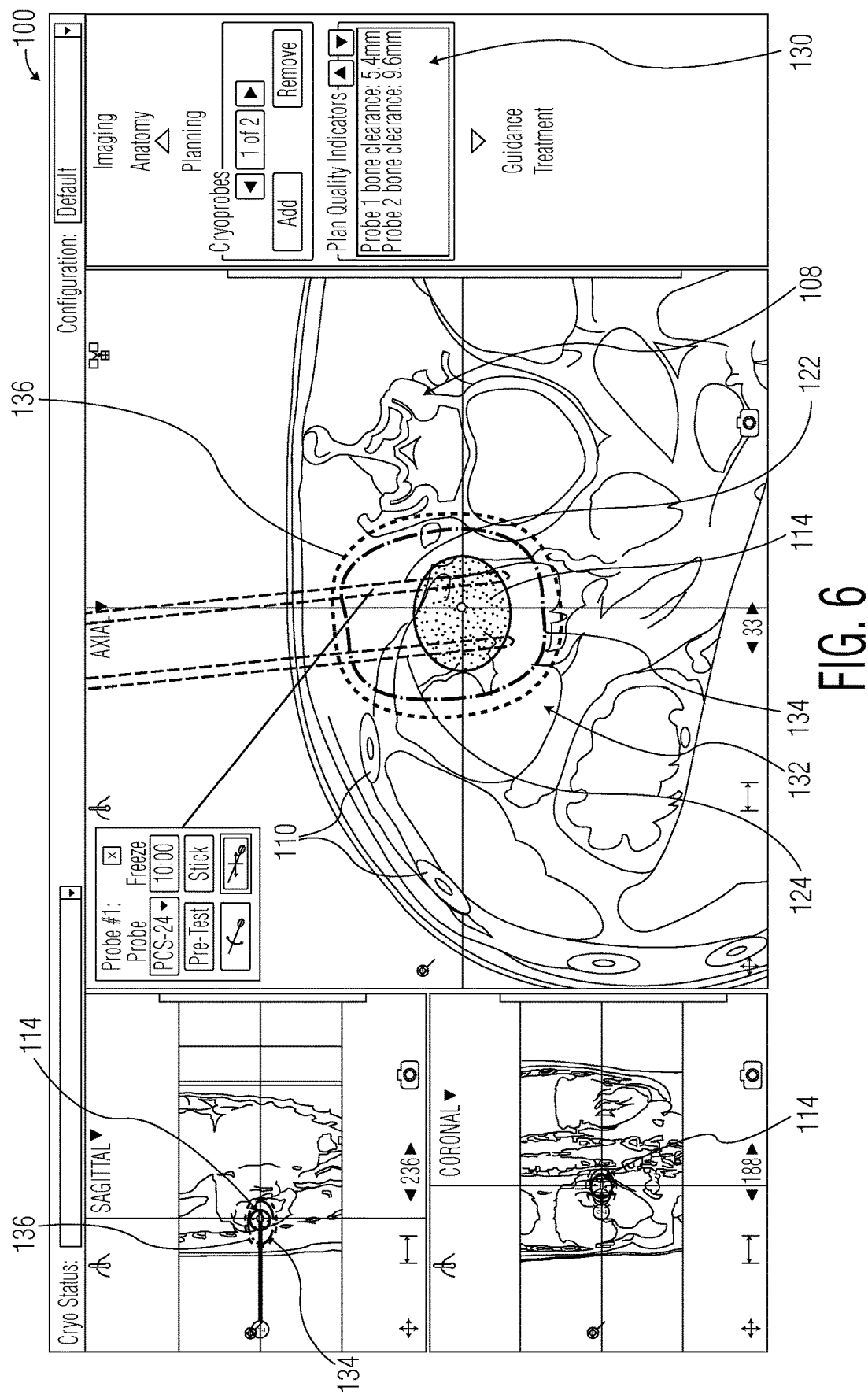
FIG. 6 depicts a three-view image on a computer device display of a treatment planning and guidance system showing combined/composite isotherms for the two separate cryoprobe isotherms shown in FIG. 5.

Because the ice balls that form as a result of the cryoprobe isotherms 126, 128 will not form separately or independently from one another and will essentially form as one composite ice ball, as can be seen in FIG. 6, the planning system calculates a generates an image depicting the size and shape of the composite isotherm/ice ball 132 for the two cryoprobes 122, 124. The system also calculates and displays the boundary of the lethal ice zone (−20° C.) 134 and the margin of the lethal ice zone (0° C.) 136, as well as other isotherm temperatures of interest depending on the tissue type and the type of procedure being performed.

At this point, the treatment plan is complete and can be finalized and saved for use with the guidance system during an ablation procedure. Also at this point, the clinician can make manual adjustments to the treatment plan based on the clinician's experience or preferences. For example, the clinician can change the location of the cryoprobes 122, 124, the orientation of the cryoprobes 122, 124, the size and shape of the target 114, etc. As a result of any clinician changes, the planning system will reflect these changes by, for example, revising the size and shape of the isotherms 134, 135 for each cryoprobe and hence, the size and shape of the composite isotherms/ice ball 132. The system's ability to compensate for such changes by updating the treatment plan will be discussed in more detail below.

Turning now to treatment guidance. On the day of the ablation procedure, the previously developed treatment plan is entered/uploaded into the guidance system. In some embodiments of the present invention, as can be seen in FIG. 1, the patient 34 is positioned in a CT suite and current CT-fluoro image data (3 or more CT-slices) is obtained. In some embodiments, the imaging device 36 is connected to the primary ablation computer 38, which is programmed with software configured to run the guidance system, such that the CT-fluoro image data can be directly uploaded into the guidance system. After the current CT-fluoro image data (3 or more CT-slices) is received by the guidance system, the guidance system performs CT fusion. That is, the guidance system is configured with software that registers the current CT-fluoro image data with/to the treatment plan image date (the baseline CT image data) that was previously developed by the clinician with the treatment planning system and uploaded to the guidance system. This registration process essentially superimposes the current CT-fluoro image data onto the baseline CT image data by aligning the same structures in each data set with each other. The basis of the fusion is the use of known algorithms that aid in the registration process. The system though, may also use a combination of algorithms including, but not limited to, mutual information, fiducial markers, manual input, etc., in order to develop an optimal super-position for fusion and therefore, an accurate registration of image data.

At this point, the clinician can compensate for any changes or differences between the two image data sets (the image data sets from the treatment plan previously developed and the current image data sets), which can be seen now that the registration process is complete, e.g., the clinician can update the treatment plan. For example, if the treatment region, which may be, for example, a tumor, has grown or has otherwise changed size and shape and the resulting ice ball formed based on the original treatment plan no longer covers the entire tumor or organs adjacent to the treatment region such as the bladder may be a different size and shape because it may now be void of urine whereas when the treatment plan was developed, it may have been full of urine, causing the treatment region to change its size and or position, the guidance system allows the clinician to change/adjust the size and shape of the target 114, which, for example, may warrant (i) a change to the position and location of the cryoprobes 122, 124 and/or (ii) modification of the shape and size of the resulting composite isotherms and the associated ice ball. All of these changes are indicated on the computer in the axial view 102, sagittal view 104 and coronal view 106. Also, the Plan Quality Indicators may change and may indicate that the new cryoprobe placement locations are no longer a safe distance from surrounding anatomy. Therefore, the clinician may have to manually change the position/location of the cryoprobes. This process can continue until the clinician is satisfied that the resulting ice ball is sufficient to "kill" the tumor while not damaging the surrounding tissue/anatomy.

Figure 7:
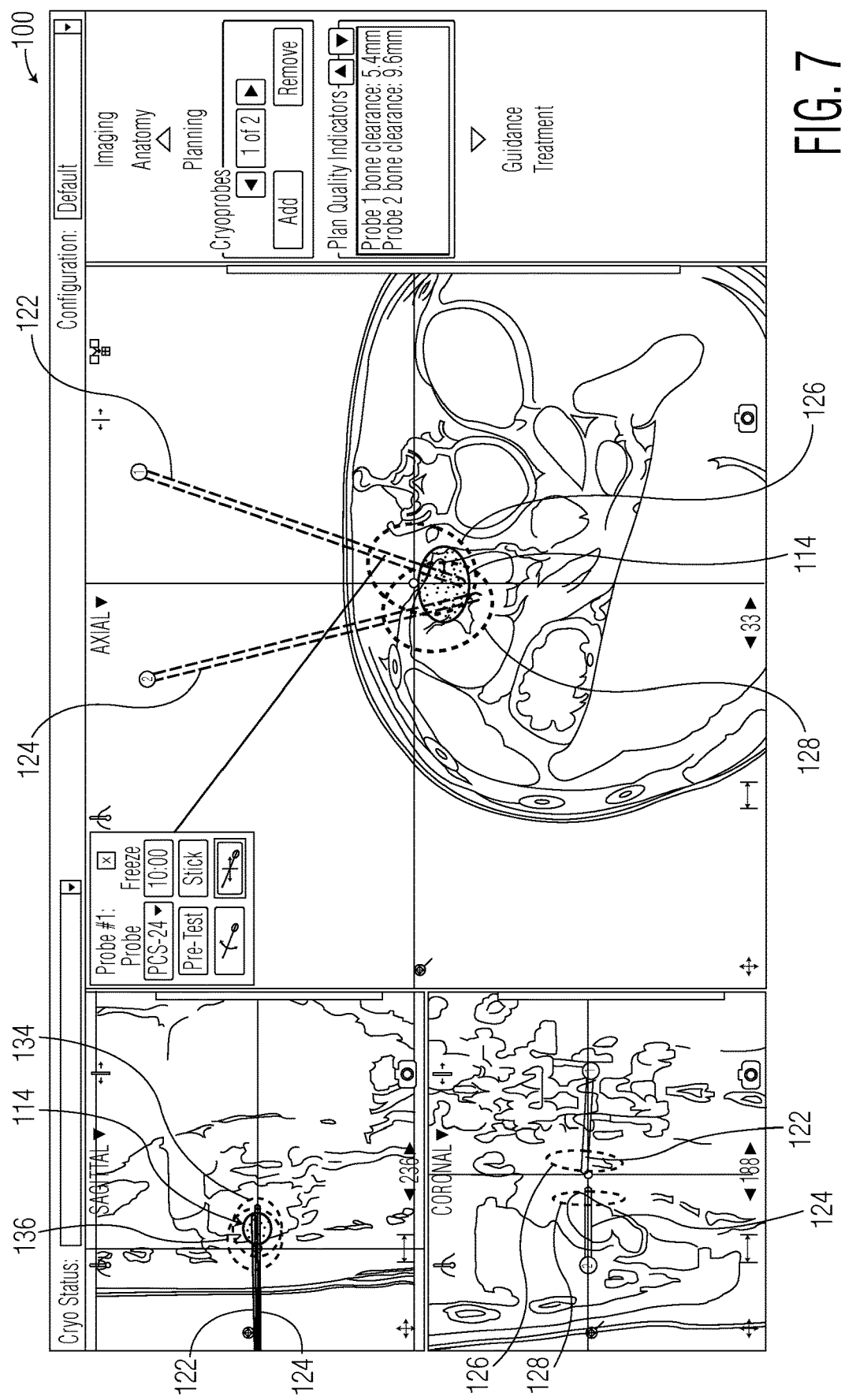
FIG. 7 depicts a three-view image on a computer device display of a treatment planning and guidance system showing revised positioning of the two separate cryoprobes and the revised individual isotherms for the two cryoprobes depicted in FIG. 5, according to an embodiment of the present invention.
Figure 8:
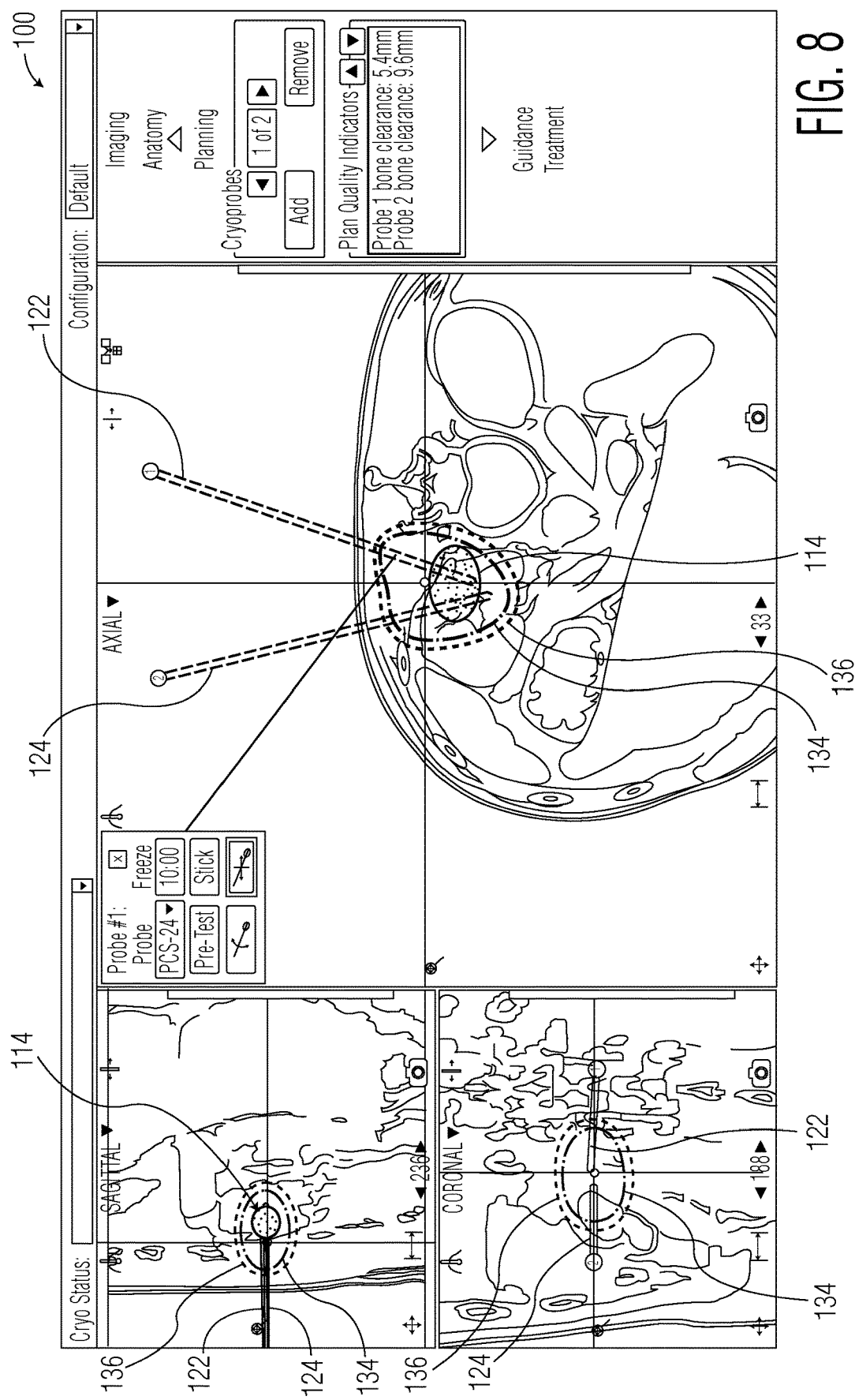
FIG. 8 depicts a three-view image on a computer device display of a treatment planning and guidance system showing combined/composite isotherms for the two separate cryoprobe isotherms shown in FIG. 7.

As depicted in FIG. 7, if the clinician changes the location and/or insertion angle of the cryoprobes 122, 124, the size, shape and position of each cryoprobe's individual isotherms 126, 128 also changes. As depicted in FIG. 8, as a result of the change in size, shape and position of the individual isotherms 126, 128, new composite isotherms 134, 136 and hence the size of the resulting composite ice ball, are automatically generated by the system. Changes to cryoprobe positioning and isotherm modeling can also occur as a result of the clinician changing the size and shape of the target 114.

Figure 9:
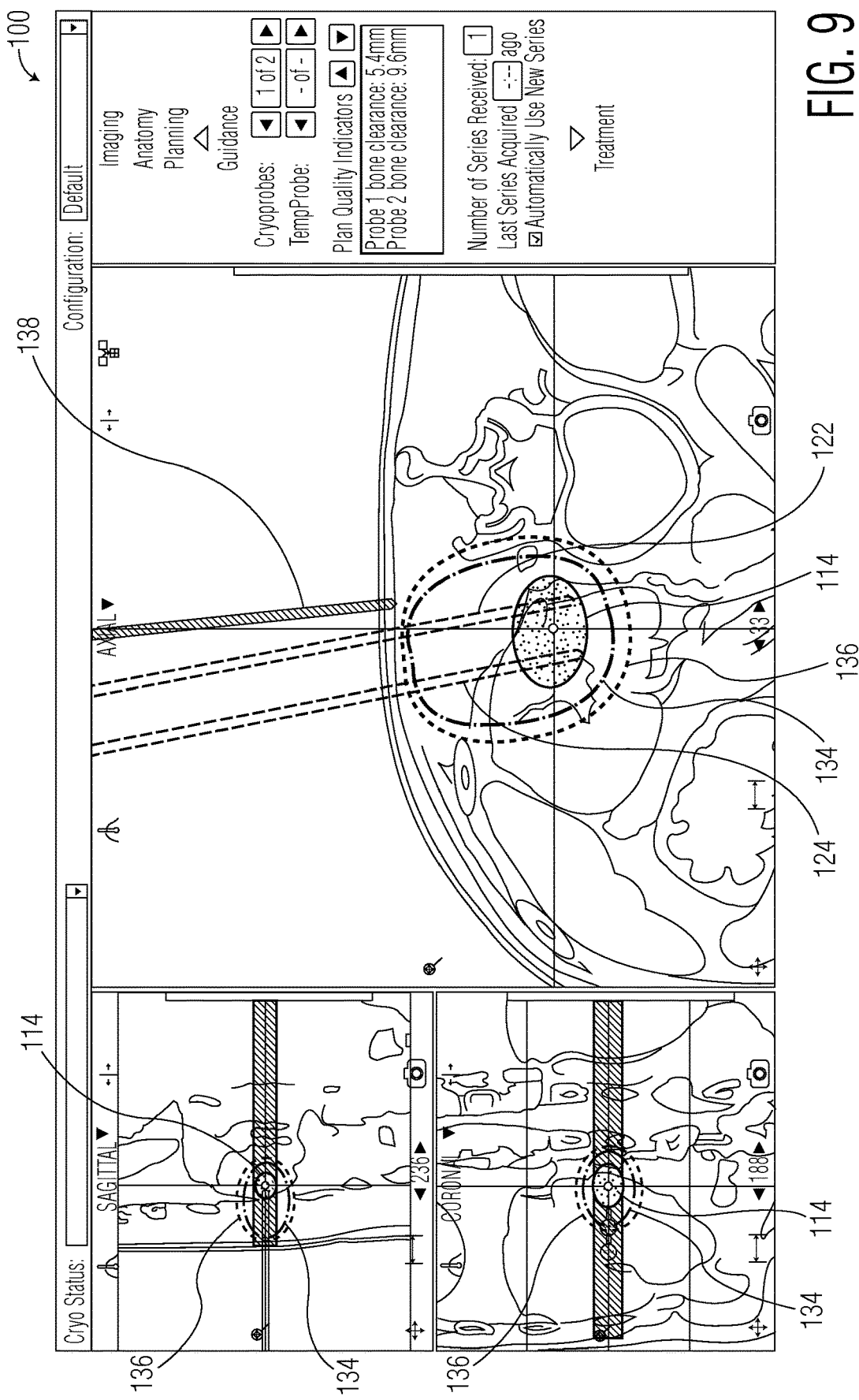
FIG. 9 depicts a three-view image on a computer device display of a treatment planning and guidance system showing partial insertion of a cryoprobe, according to an embodiment of the present invention.

Once the clinician is satisfied with the updated treatment plan, the clinician can then start the ablation procedure by beginning to insert the first cryoprobe. During the insertion process, the clinician does not completely insert the first cryoprobe. Instead, as depicted in FIG. 9, the clinician partially inserts the actual cryoprobe 138 and then obtains additional CT-fluoro image data (3 or more CT-slices) using the imaging device 36. After the additional CT-fluoro image data is received by the guidance system, the system performs the CT fusion process discussed above by registering the newly-received CT-fluoro image data with/to the baseline CT image data. At this juncture of the process, if needed, the system may also use cryoprobe positioning from the CT-fluoro image data as part of its fusion process. This newly registered CT-fluoro image data is now displayed s the three-view image depicted in FIG. 9, which shows that the actual cryoprobe 138 was not placed according to the calculated cryoprobe placement 122 of the treatment plan.

Figure 10:
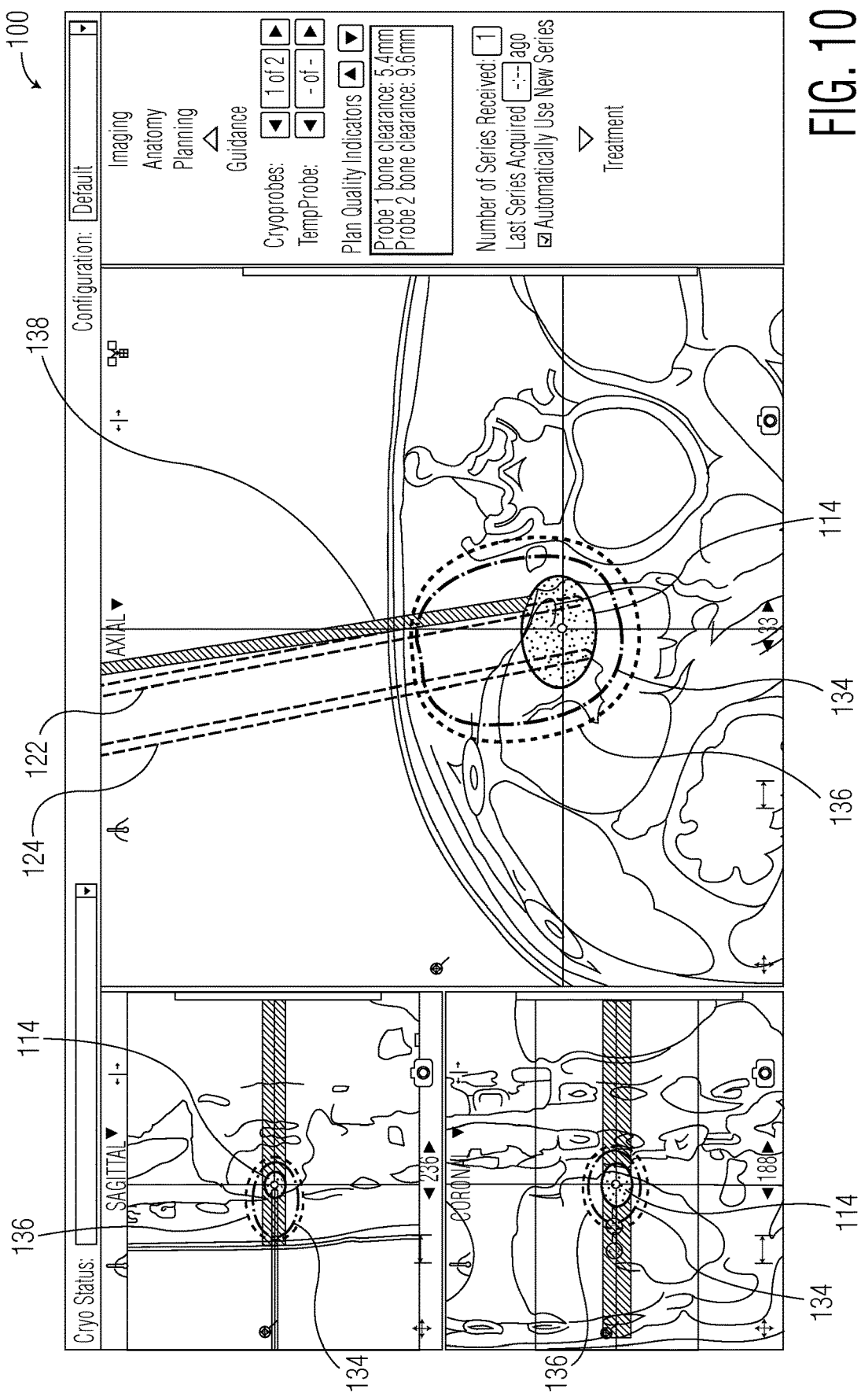
FIG. 10 depicts a three-view image on a computer device display of a treatment planning and guidance system showing complete insertion of a cryoprobe, according to an embodiment of the present invention.
Figure 11:
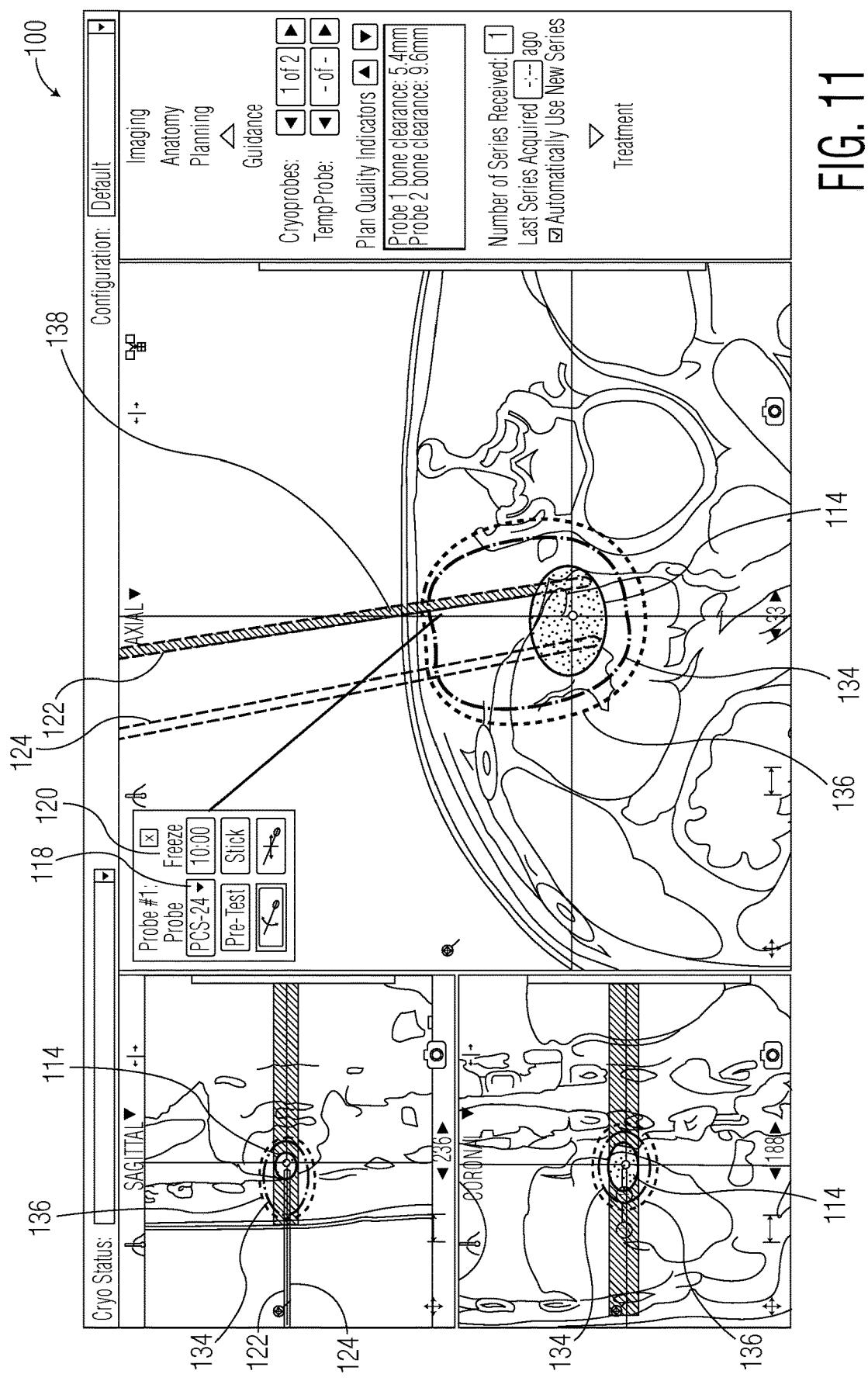
FIG. 11 depicts a three-view image on a computer device display of a treatment planning and guidance system showing a revised treatment plan in response to updating the planned position of the inserted cryoprobe depicted in FIG. 10.

Now that the clinician can see that the actual cryoprobe 138 placement is not in accordance with the planned cryoprobe 122 placement, the clinician can attempt to correct this misalignment as the actual cryoprobe 138 is inserted further into the treatment region (target 114) by altering the cryoprobe's 138 orientation/insertion angle during insertion. To aid in the accuracy of cryoprobe insertion, the clinician can obtain additional CT-fluoro image data during the cryoprobe insertion process where the system performs the CT fusion process discussed above by registering any newly-received CT-fluoro image data with/to the previously acquired images. After the clinician inserts the actual cryoprobe 138 all the way to its final position, the clinician obtains additional CT-fluoro image data (3 or more CT-slices) using the imaging device 36. After the additional CT-fluoro image data is received by the guidance system, the system performs the CT fusion process discussed above by registering the newly received CT-fluoro image data with/to the previously acquired image data. This newly-registered CT-fluoro image data of the final placement of the first cryoprobe 138 can be seen in FIG. 10, which shows that the actual final position of the cryoprobe 138 is closer to the planned cryoprobe 122 placement position but was still not placed exactly according to the treatment plan. Therefore, at this point, the clinician can again revise the treatment plan by repositioning the planned cryoprobe 122 placement so that it coincides exactly with the actual cryoprobe 138 placement as depicted in FIG. 11. This repositioning can be performed by the clinician, for example, by simply manipulating the planned cryoprobe 122 placement on the display with the aid of a user interface such as, for example, an electronic pen, a mouse or any other user interface known in the art. Other manipulation methods and devices will be readily understood and known by those of skill in the art.

It should be noted that any CT-fluoro image data can be registered to any other CT-fluoro image data. That is, in the current embodiment, CT-fluoro image data is registered to the baseline CT image data. However, in other embodiments, the newest or most-recent CT-fluoro image data can be registered to the most previous CT-fluoro image data, which itself may have been registered to its most previous CT-fluoro image data resulting in consecutively registered image data. Or, CT-fluoro image data can be registered to any other CT-fluoro image data such that it is not registered in a consecutive manner. In addition, the final CT-fluoro image data from the date of the procedure can be registered to post-procedure image data to see if the treatment region experiences any changes, i.e., tumor growth, etc.

As can be seen in FIG. 11, the planned cryoprobe 122 placement position has been updated to correspond to the actual cryoprobe 138 placement position. As a result of this updated cryoprobe placement position, the composite isotherms 134, 136 have been updated by the system to reflect the actual cryoprobe 138 placement thereby giving the clinician accurate visual information about the isotherms 134, 136 and ice ball formation. Based on the "revised treatment plan" that resulted from updating the planned cryoprobe 122 placement to correspond with the actual cryoprobe 138 placement, the clinician can again adjust the target 114 size or the planned placement of the other cryoprobe 124 in order to change the size and shape of the composite isotherms 134, 136 and hence, the size and shape of the resulting ice ball, to compensate for the misplacement of the first cryoprobe 138. Additional adjustments that can be made to the treatment plan to compensate for any misplacement of a cryoprobe include, but are not limited to, adjusting the energy power levels and/or cryoprobe freeze times or cycle times for certain cryoprobes or all cryoprobes.

Figure 12:
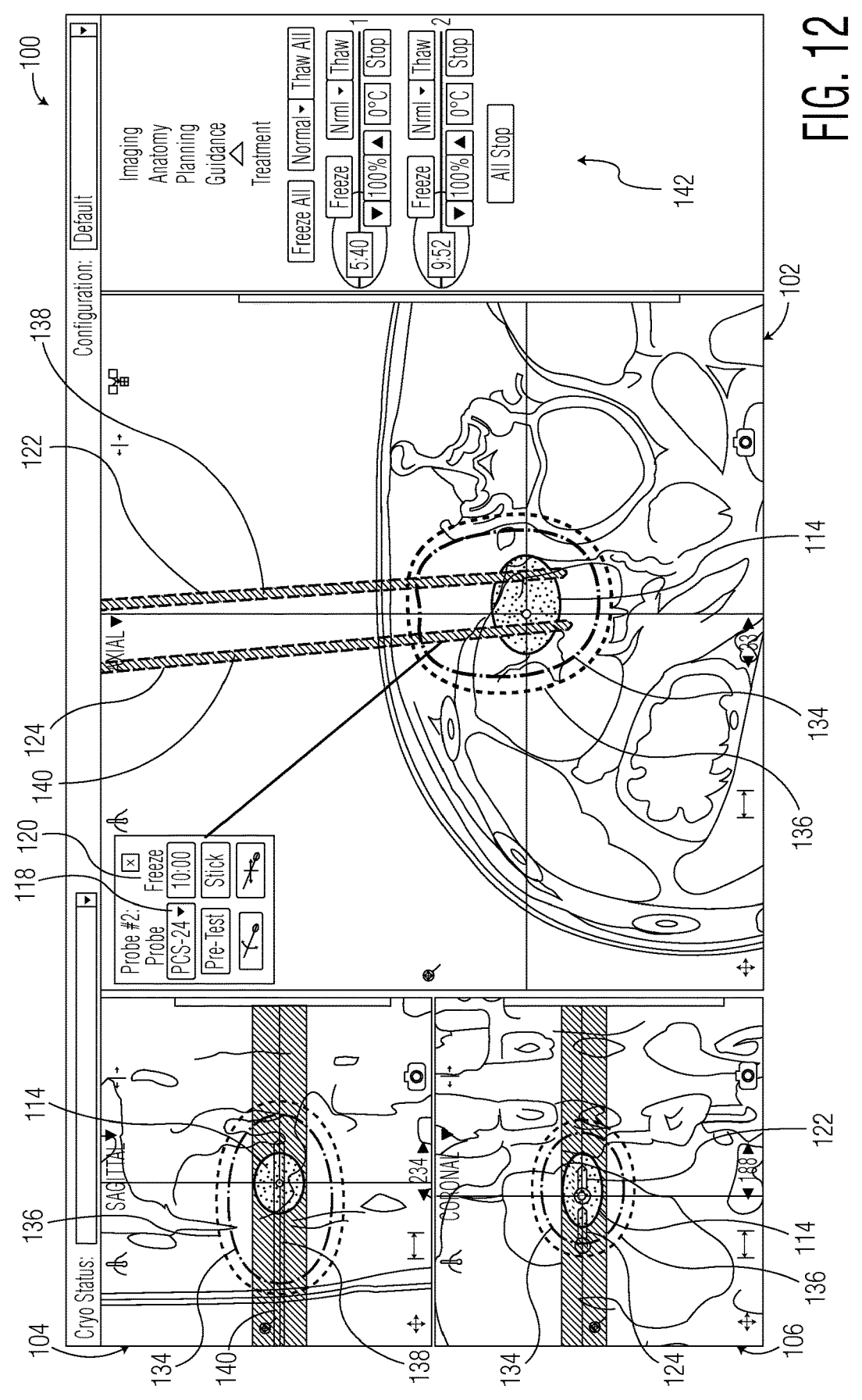

Once the two actual cryoprobes 138, 140 are inserted to their final position in the target 114, the system can be set to treatment mode as depicted FIG. 12. In treatment mode, the system runs the cryoprobes 138, 140 according to the pre-determined ablation protocols and provides the clinician with information about the cryoprobes 138, 140. For example, in some embodiments, this information 142 includes whether the cryoprobes are in "freeze" mode or "thaw" mode, the length of time that the cryoprobes have been in the "freeze" or "thaw" mode, and the power level at which each cryoprobe is operating. The "freeze" and "thaw" times and power levels can be manually adjusted by the clinician during the ablation procedure. For example, if a cryoprobe is placed closer to a certain structure or anatomy than planned, the system will provide for modeling a reduced power setting (say 80% instead of 100%) that will result in smaller isotherms. In another example of setting adjustments, the time setting may be adjusted from 10 minutes (for a 10-8-10 protocol) to a 3 minute setting (for a 3-5-3-5-5 protocol) where the first time interval is a freeze and subsequent time-intervals are for alternative thaw and freeze modes.

For certain ablation procedures, for example, procedures involving the prostate, the tendency of the anatomy to "deform" during an ablation procedure or between imaging studies, limits the utility of rigid registration techniques. Therefore, for these ablation procedures, the system includes and uses deformable registration to register images. Deformable registration provides the ability to integrate pre-treatment imaging from various modalities with imaging taken at the time of the procedure. Because changes may occur to patient anatomy between the imaging events, including those caused by a different patient position, different organ sizes and configurations (e.g. gastrointestinal or bladder filling/emptying), and changes caused by the imaging itself (e.g., displacement from an endorectal ultrasound probe in TRUS), the system applies a process of deformable registration in order to compensate and maximize clinical utility. Deformable registration propagates anatomic contours from one image set to another image set allowing the system to map targets, other anatomy, and ice ball formation from one image set to another image set.

In prostate procedures, for example, the application of deformable registration permits anatomic and target details derived from multi-parametric MR imaging acquired at a different time, potentially including interesting patient anatomy changes, such as from an ultrasound probe that is inserted into the rectum, which presses the prostate gland against the pelvic bones thereby deforming or displacing the treatment region (prostate). Due to normal organ motion and deformation, and the motion and deformation caused by movement of the ultrasound probe, deformable registration is the ideal method for registering image data during a prostate ablation procedure. Thus, because deformable registration addresses these deformations of the treatment regions (targets), deformable registration may also be preferable in ablation cases in which the target 114 deforms as a result of the introduction of a cryoprobe or which have a tendency to deform over time.

In one embodiment of the current system, deformable registration is performed by transforming one dataset so that the contours defined in it match the surface inferred from the contours defined in the second dataset. Contours in the system are planar loops which can be defined on multiple planes, each of which is either parallel or perpendicular to all others, and which may be edited in any order.

Determination of whether two surfaces match requires quantifying the uncertainty of the surface position in between the planar contours. This determination includes both the distance between contour planes and the actual distance between contour points. The latter is computed and stored for a given voxel as the minimum number of adjacent voxels connecting the given voxel with a boundary voxel, passing only through voxel faces. This arrangement permits a rapid assessment of the total "distance-to-match" yielded by a candidate transform. In order to satisfy the requirement to relate anatomy from the registered series other than the anatomy that drove the registration process (e.g., tumor contours within or adjacent to a registered prostate), the transform used provides for interpolation and extrapolation to transform any coordinate. Note that this conversion involves a non-trivial surface inference in order to get back to planar contour sets at image locations, and this inference algorithm will be discussed further below. This conversion can also discard information about the transform, and the registered series, particularly if that series is sliced more densely than the baseline series, as will often be the case in MR-TRUS registrations where the TRUS imaging will serve as the treatment baseline.

To optimize the transform, the process begins with a translation that brings the centers of the two contour sets together. Next, a 6-DOF simplex optimization calculates 3D translations and rotations, according to the metric described above. An additional optimization run is then performed with smaller characteristic lengths for the translations and rotations, and with an added 3-DOF for scaling. The resulting gross transform is then fine-tuned with local deformations. During this tuning process an octree displacement field is interpolated (tri-linear) to find displacements at individual nodes. The octree nodes are individually optimized with 3-DOF, considering only those baseline contour points that lie within half the internode distance of the node center at that resolution level, but otherwise using the same metric as above. This process is repeated across nodes, and at successively smaller resolution steps until all baseline contour points in the region (i) map to registered series contour points or (ii) the inter-octree-node distance crosses below a configurable detail threshold (in one embodiment, set to 5 mm). Having been transferred to the contour nodes, the octree displacements are saved for later use. Each contour is then scanned for stretches of nodes above the threshold distance in the requirement. For each such stretch a recursive binary subdivision is performed in which the central node's displacement is set according to an interpolation of its neighboring sub-threshold nodes and adjusted to map it to the nearest sub-threshold point from that location. In this way, all baseline contour nodes are mapped to an edge point in the registered series, using a displacement field defined all along the organ boundary.

In order for the displacement field to be evaluated inside the contour sets, and so the registered series can be reformatted to coincide with baseline voxel positions, the boundary displacements and octree nodes are used to create a volumetric displacement field according to the following rules:

Points contained within an octree node without contour points are derived by tri-linear interpolation of adjacent octree node centers; and Other points are calculated according to a weighted average displacement based on the displacements of all contour nodes within the octree node, weighted according to their inverse squared Cartesian distance from the sample point.

Every pair of contour sets on adjacent slices creates bounds to a surface segment with potentially arbitrary complexity and ambiguity, such as bifurcations or disjoint regions in the gap. A surface interpolation algorithm makes anatomically appropriate assumptions in these regions. The algorithm employed in this embodiment creates a planar region corresponding to the area enclosed by one, but not both, of the adjacent contour sets, and assigns a fraction of the inter-slice gap from image A to image B to points within the new region according to the ratio of the previously computed distance map generated for image A to the sum of the distance metrics for that point in both images. The resulting height map describes the surface in the gap between those slices, and the process can be repeated throughout the series.

After the images from the prostate procedure are deformably registered using the above-described process or other deformable registration process known in the art, the system functions as described above for rigidly registered image data.

Figure 13:
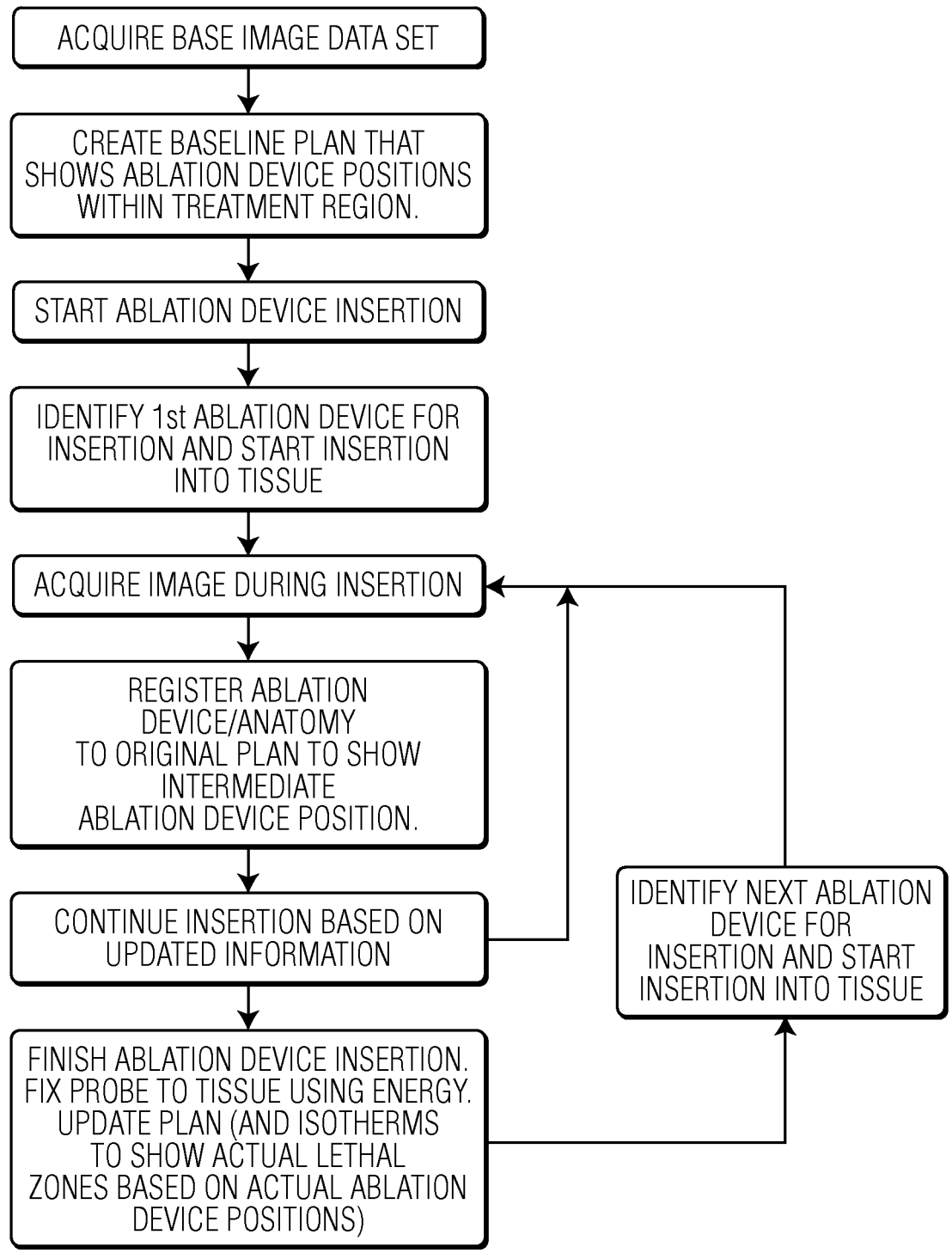
FIG. 13 is a flow diagram of a method of planning, guiding and performing an ablation procedure, according to an embodiment of the present invention.

FIG. 13 is a flow diagram depicting a method of planning, guiding and performing an ablation procedure.

As discussed herein, embodiments of the present invention allow a clinician to intra-operatively adjust the positioning/placement of ablation devices. By having the ability to intra-operatively adjust the ablation device positions, the physician/clinician can guide the ablation devices to the optimal position. In addition, by knowing the difference between the final position of each device and its planned position, the physician/clinician can adjust the ablation settings for that device and/or adjust the planned placement for each consecutive ablation device to be inserted based on the previous ablation device position so as to achieve optimum ablation device positioning and hence, optimal lethal ablation zone formation. This ability will result in more efficient ablation procedures with better and more certain outcomes. The system allows the surgeon to adjust settings in multiple ways.

Post placement of the cryoprobes, the clinician monitors the growth of the ice ball. The system will import images from an imaging device, register those images to the most recent treatment/guidance plan and display the registered position to the actual position so that the clinician can verify the treatment against the recent plan.

Although the present invention has been described above in terms of exemplary embodiments, it is not limited thereto. Rather, the appended numbered paragraphs should be construed broadly to include other variants and embodiments of the invention which may be made by those skilled in the art without departing from the scope and range of equivalents of the invention.

What is claimed is:

1. A system for assisting a surgeon in placing at least one ablation device into a treatment region of a patient, the system comprising:
    at least one computer system comprising a display, a user interface and software configured to:
        receive patient image data of the treatment region;
        generate an image of the treatment region on the display;
        identify the treatment region to ablate with a target;
        identify the type(s) of tissue within the treatment region;
        identify patient anatomy surrounding the treatment region;
        identify the type(s) of tissue surrounding the treatment region;
        identify the thermal properties of the type(s) of tissue both within the treatment region and of the anatomy surrounding the treatment region including the heat capacity, thermal conductivity, and metabolic heat generation of the type(s) of tissue;
        perform thermal modeling of the treatment region and the anatomy surrounding the treatment region based on the identified thermal properties;
        generate treatment parameters for the at least one ablation device;
        calculate a number of ablation devices required to ablate the treatment region and a location and orientation of each ablation device in the treatment region based on a size of the target and the thermal modeling of the treatment region and anatomy surrounding the treatment region;
        calculate an ablation zone based on the number of ablation devices required to ablate the treatment region, the location and orientation of each ablation device in the treatment region, and the thermal modeling of the treatment region and anatomy surrounding the treatment region; and
        display on the computer system display (a) the number of ablation devices required to ablate the treatment region and the location and orientation of each ablation device in the treatment region and (b) the ablation zone.

2. The system of claim 1, wherein the patient image data is CT-fluoro image data.

3. The system of claim 1, wherein the at least one ablation device is a cryoprobe.

4. The system of claim 1, wherein the system is for assisting the surgeon in placing at least two ablation devices into the treatment region of the patient, the at least two ablation devices are cryoprobes, and the ablation zone includes a composite isotherm comprising individual isotherms for each of the number of cryoprobes calculated to ablate the treatment region.

5. The system of claim 1, wherein the software is further configured to allow the surgeon to revise the number of ablation devices required to ablate the treatment region and/or the location and/or the orientation of each ablation device in the treatment region.

6. The system of claim 1, wherein the image of the treatment region comprises an axial view, a sagittal view and a coronal view.

7. The system of claim 1, wherein the ablation devices are cryoprobes, the number of ablation devices is two cryoprobes, and the ablation zone includes a composite isotherm comprising individual isotherms for each of two cryoprobes calculated to ablate the treatment region.

8. The system of claim 1, wherein the target that identifies the treatment region to ablate is generated by:
    placing the target at a point within the treatment region;
    determining the density of the tissue at the point within the treatment region; and
    expanding the target to tissue surrounding the point within the treatment region that has the same density as that determined for the tissue at the point within the treatment region.

9. The system of claim 1, wherein each of the thermal properties, including the heat capacity, thermal conductivity, and metabolic heat generation, are modeled as a linear function for temperatures above zero degrees Celsius and another linear function for temperatures below zero degrees Celsius.

10. A method of developing an ablation treatment plan comprising the steps of:
receiving patient image data of a treatment region;
generating an image of the treatment region on a display;
identifying the treatment region to ablate with a target;
identifying the type(s) of tissue within the treatment region;
identifying patient anatomy surrounding the treatment region;
identifying the type(s) of tissue surrounding the treatment region;
identifying the thermal properties of the type(s) of tissue both within the treatment region and of the anatomy surrounding the treatment region including the heat capacity, thermal conductivity, and metabolic heat generation of the type(s) of tissue;
performing thermal modeling of the treatment region and the anatomy surrounding the treatment region based at least in part on the identified thermal properties;
determining treatment parameters for at least one ablation device;
calculating a number of ablation devices required to ablate the treatment region and a location and orientation of each ablation device in the treatment region based on a size of the target and the thermal modeling of the treatment region and anatomy surrounding the treatment region;
calculating an ablation zone based on the number of ablation devices required to ablate the treatment region, the location and orientation of each ablation device in the treatment region, and the thermal modeling of the treatment region and anatomy surrounding the treatment region; and
displaying on the display (a) the number of ablation devices required to ablate the treatment region and the location and orientation of each ablation device in the treatment region and (b) the ablation zone.

11. The method of claim 10, wherein the step of performing thermal modeling further comprises adjusting the thermal properties of the tissue in the treatment region by inferring a contribution from the tissue's water content.

12. The method of claim 10, wherein the number of ablation devices is at least two ablation devices, the ablation devices are cryoprobes, and the ablation zone is calculated from a composite isotherm formed from individual isotherms of each of the cryoprobes.

13. The method of claim 10, wherein the number of ablation devices is two ablation devices, the ablation devices are cryoprobes, and the ablation zone is calculated from a composite isotherm formed from individual isotherms of each of the two cryoprobes.

14. A system for guiding and performing an ablation procedure on a treatment region of a patient, the system comprising:
at least one computer system comprising a display, a user interface and software, the at least one computer system configured to:
receive an ablation treatment plan comprising (a) a treatment plan set of patient image data, (b) a number of ablation devices required to ablate the treatment region and the location and orientation of each ablation device in the treatment region and (c) boundaries of an ablation zone; wherein the number of ablation devices required to ablate the treatment region and the location and the orientation of each ablation device in the treatment region is based on a thermal modeling of the treatment region performed based on tissue properties of both the treatment region and the tissue surrounding the treatment region, wherein the tissue properties include heat capacity, thermal conductivity, and metabolic heat generation; and the boundaries of the ablation zone are based on the number of ablation devices required to ablate the treatment region, the location and orientation of each ablation device in the treatment region, and the thermal modeling;
receive at least one set of patient image data of the treatment region taken on a day of the ablation procedure;
register the at least one set of patient image data of the treatment region taken on the day of the ablation procedure to the treatment plan set of patient image data;
allow adjustment of a size and/or shape and/or location of the treatment region based on the registered at least one set of patient image data of the treatment region taken on the day of the ablation procedure to the treatment plan set of patient image data;
recalculate the number of ablation devices required to ablate the treatment region and the location and the orientation of each ablation device in the treatment region based on any adjustments to the size and/or shape and/or location of the target based on the registered first set of patient image data and the second set of patient image data;
update the ablation zone based on the recalculated number of ablation devices required to ablate the treatment region and/or the recalculated location and/or the recalculated orientation of each ablation device in the treatment region; and
update the display on the computer system to display (a) the recalculated number of ablation devices required to ablate the treatment region and/or the recalculated location and/or the recalculated orientation of each ablation device in the treatment region and (b) the remodeled ablation zone;
an ablation energy generator; and
at least one ablation device.

15. The system of claim 14, wherein the at least one ablation device is selected from the group consisting of cryoprobes, laser fibers, RF electrodes, microwave antennas and high-intensity focused ultrasound devices.

16. The system of claim 14, wherein the ablation energy generator is a cryoengine.

17. The system of claim 16, wherein a cryogenic fluid is selected from the group consisting of argon and nitrogen.

18. The system of claim 14, wherein the number of ablation devices is at least two ablation devices, the ablation devices are cryoprobes, and the boundaries of the ablation zone including the size and shape of a composite isotherm formed from individual isotherms for each cryoprobe.

19. The system of claim 14, wherein the number of ablation devices is two ablation devices, the ablation devices are cryoprobes, and the boundaries of the ablation zone including the size and shape of a composite isotherm formed from individual isotherms for each of the two cryoprobes.

20. The system of claim 14, wherein the registration of the at least one set of patient image data of the treatment region taken on the day of the ablation procedure to the treatment plan set of patient image data is deformable registration.

* * * * *